United States Patent [19]
Hoag et al.

[11] Patent Number: 6,120,174
[45] Date of Patent: Sep. 19, 2000

[54] APPARATUS AND METHOD FOR MIXING AND DISPENSING BONE CEMENT

[75] Inventors: Stephen H. Hoag; Kirt L. Case, both of Warsaw, Ind.; Kwan-Ho Chan, Lubbock, Tex.; Jeffrey B. Boggs, Dover, Ohio; Christopher A. Finn, Dover, Ohio; Scott B. Miller, Dover, Ohio

[73] Assignee: Bristol-Myers Squibb, New York, N.Y.

[21] Appl. No.: 09/231,894

[22] Filed: Jan. 14, 1999

[51] Int. Cl.$^7$ .................................................... B01F 13/06
[52] U.S. Cl. ........................................... 366/139; 366/255
[58] Field of Search ...................... 366/129, 130, 366/139, 255, 256; 604/416; 222/327

[56] References Cited

U.S. PATENT DOCUMENTS

| | | | |
|---|---|---|---|
| Re. 35,276 | 6/1996 | Chan | 366/139 |
| 1,718,603 | 6/1929 | Smith . | |
| 1,744,449 | 1/1930 | Dawson . | |
| 1,819,258 | 8/1931 | Nevin . | |
| 2,453,914 | 11/1948 | Hollenback . | |
| 2,696,022 | 12/1954 | Steinbock et al. | 366/139 |
| 2,838,392 | 6/1958 | Bielawski | 75/5 |
| 2,973,187 | 2/1961 | Wehmer . | |
| 3,131,912 | 5/1964 | Steinbock, Jr. . | |
| 3,164,303 | 1/1965 | Trautmann | 222/190 |
| 3,343,817 | 9/1967 | Carangelo et al. | 259/122 |
| 3,358,971 | 12/1967 | Steinbock | 366/139 |

(List continued on next page.)

FOREIGN PATENT DOCUMENTS

| | | |
|---|---|---|
| 0178658 | 4/1986 | European Pat. Off. . |
| 319921 | 3/1962 | France ................................. 366/332 |
| 8403830 | 11/1984 | Japan . |
| 86/06618 | 11/1986 | WIPO . |

OTHER PUBLICATIONS

MIT VAC, "Vacuum Mixing System", *Mitab*, (Article) (date unknown).

Zimmer, "Vacuum Mixing System", Z (Article) (1986).

Depuy Vacu–Mix, "Orthopedic Cement Mixing system" (Apr. 1977).

Stryker, "Simple, Sterile, Disposable MixEvac" (Aug. 1978).

Howmedica, "The Simplex Enhancement Vacuum Mixer", No. 2 *JBJS* 69–A Feb. 1987.

Zimmer, "Cement Centrifugation System", (Article) (1984, month unknown).

*Primary Examiner*—Tony G. Soohoo
*Attorney, Agent, or Firm*—Cary R. Reeves

[57] ABSTRACT

A method and apparatus for mixing bone cement which produces bone cement essentially free of entrained air. The apparatus includes a cartridge having two telescoping cylinders. The outer cylinder receives a cap thereon which hermetically seals the cartridge. The cap includes an outlet port in which a break-away agitator is installed and a port for connection of a vacuum pump. In use, a desired vacuum pressure is drawn on the cartridge and the inner cylinder is allowed to be drawn into the outer cylinder while the vacuum is being drawn, whereupon the inner cylinder automatically stops moving relative to the outer cylinder when the desired vacuum pressure is reached. Mixing of the bone cement is then performed under the partial vacuum thereby created. The agitator paddles provide a scraping action against both inner cylinder walls of the telescoping cylinders thereby improving mixing. After mixing, the agitator is broken away, an appropriate nozzle is attached to the cartridge and the cartridge is inserted into a cement gun. The leading portion of the bone cement develops a convex profile when axially advanced through the cartridge and the piston plug includes a tapered protrusion which generally corresponds to the profile of the bone cement. The cap and paddles are also shaped correspondingly to the convex profile developed by the bone cement, resulting in substantially all of the bone cement being squeezed from the cartridge. An air escape passage is also provided to vent air contained within an annular gap between the agitator shaft and the cap upon initial being essentially free from entrained air.

8 Claims, 8 Drawing Sheets

U.S. PATENT DOCUMENTS

| | | |
|---|---|---|
| 3,366,369 | 1/1968 | Ravasi . |
| 3,559,961 | 2/1971 | Bergendal . |
| 3,560,162 | 2/1971 | Mittleman ................. 23/253 |
| 3,565,168 | 2/1971 | Powell et al. ............... 163/83 |
| 3,610,586 | 10/1971 | Price et al. . |
| 3,640,510 | 2/1972 | Lea . |
| 3,946,996 | 3/1976 | Gergely . |
| 3,988,499 | 10/1976 | Reynolds ................. 428/474 |
| 4,185,072 | 1/1980 | Puderbaugh et al. ............ 422/99 |
| 4,197,967 | 4/1980 | Baur et al. ................. 366/256 |
| 4,199,153 | 4/1980 | Martin ..................... 277/4 |
| 4,199,866 | 4/1980 | Drury ..................... 366/139 |
| 4,277,184 | 7/1981 | Solomon ................... 366/150 |
| 4,338,925 | 7/1982 | Miller ..................... 128/92 |
| 4,426,022 | 1/1984 | Lang et al. ................. 222/130 |
| 4,463,875 | 8/1984 | Tepic . |
| 4,551,135 | 11/1985 | Gorman et al. ............... 604/82 |
| 4,605,129 | 8/1986 | Detzel et al. ................ 206/623 |
| 4,671,263 | 6/1987 | Draenert .................... 128/92 |
| 4,676,406 | 6/1987 | Frischmann et al. ........... 222/136 |
| 4,721,390 | 1/1988 | Lidgren .................... 366/139 |
| 4,735,509 | 4/1988 | Rausch ..................... 366/333 |
| 4,743,229 | 5/1988 | Chu ........................ 604/82 |
| 4,758,096 | 7/1988 | Gunnarsson ................. 366/139 |
| 4,787,751 | 11/1988 | Bakels ..................... 366/110 |
| 4,799,801 | 1/1989 | Brüning ................... 366/255 |
| 4,808,184 | 2/1989 | Tepic ...................... 604/56 |
| 4,854,716 | 8/1989 | Ziemann et al. ............. 366/139 |
| 4,858,759 | 8/1989 | Mauthe et al. .............. 206/221 |
| 4,961,647 | 10/1990 | Coutts et al. .............. 366/139 |
| 4,973,168 | 11/1990 | Chan ....................... 366/139 |
| 5,100,241 | 3/1992 | Chan ....................... 366/139 |
| 5,121,990 | 6/1992 | Guiet et al. ............... 366/139 |
| 5,252,301 | 10/1993 | Nilson et al. .............. 366/256 |
| 5,501,520 | 3/1996 | Lidgren et al. ............. 366/139 |
| 5,551,778 | 9/1996 | Hauke et al. ............... 366/139 |
| 5,624,184 | 4/1997 | Chan ....................... 366/139 |
| 5,779,356 | 7/1998 | Chan ....................... 366/139 |
| 5,788,463 | 8/1998 | Chan ........................ 417/63 |
| 5,829,875 | 11/1998 | Hagel et al. ............... 366/256 |

6,120,174

APPARATUS AND METHOD FOR MIXING AND DISPENSING BONE CEMENT

BACKGROUND OF THE INVENTION

This invention relates generally to apparatus for mixing and dispensing bone cement. In particular, this invention relates to improvements to a disposable preassembled kit including a collection of preparation apparatus used to mix and dispense bone cement. The improvements are directed toward eliminating entrained air in the mixed cement and improving the mixing and dispensing characteristics.

In many orthopaedic surgical procedures, bone cements are used to fix implants to the bone. Conventional bone cements are generally polymeric materials which are prepared by copolymerization of the components as needed. Bone cement is prepared by copolymerizing a liquid monomer and a powdered copolymer, such as methyl methacrylate and polymethyl methacrylate or methyl methacrylate-styrene. During mixing of the constituent components of the cement, air bubbles may be formed within the cement. It is thought that to improve the resultant strength of the cement, the air bubbles must be evacuated from the mixture to ensure a uniform reaction product. Consequently, the mixing of the constituent components is ideally performed in a vacuum.

Mixing separate constituent components within a mixing cartridge is well-known in the art. For example, U.S. Pat. Nos. 5,624,184 and 5,586,821, which are assigned to the assignee of the present invention and are hereby incorporated by reference, disclose a mixing cartridge comprising two telescoping tubular cylinders. The telescoping cylinders are positionable into a fully extended position in which the bone cement components are mixed under vacuum, a vacuum release position in which the inner cylinder is partially retracted within the outer cylinder, and a fully retracted position in which the cartridge is adapted for installation into a bone cement mixing gun. A cap is installed on the proximal end of the outer cylinder and includes an opening therethrough which receives the shaft of an agitator. The cap also includes a port for connection thereto of a vacuum pump which is used to draw a vacuum in the cartridge when in the fully extended position. The portion of the agitator shaft which extends into the cartridge includes agitator paddles extending therefrom for mixing the bone cement. The other end of the agitator shaft which extends from the opening in the cap includes a handle thereon for reciprocating movement of the agitator within the cartridge. The shaft includes a tubular outer sleeve and an inner rod axially disposed therein which terminates in an integral dumbbell-shaped end plug. The shaft sleeve is frangible and has a detachable distal end, so that after mixing is completed, the shaft can be broken away from the cap along with the inner rod. This results in the opening in the cap retaining the distal end of the shaft having the agitator paddles integrally connected thereto. A suitable cement nozzle can then be affixed to the opening (outlet port), and the cartridge inserted into an applicator gun. The inner cylinder includes a piston plug which is axially movable toward the cap end of the cartridge by operating the cement gun.

In use, the above described cartridge is initially fully extended and the bone cement constituents are placed therein. Thereupon, the cap is installed on the outer cylinder and a vacuum pump is attached to the outlet port contained on the cap. A vacuum is drawn on the cartridge by reciprocating the handle on the vacuum pump. The bone cement components are then mixed under a partial vacuum by reciprocating the agitator handle. After mixing is completed, the inner cylinder is partially retracted within the outer cylinder which releases the hermetic seal therebetween and thereby causes the vacuum to be released. The cartridge is then positioned into its fully retracted position and installed into an applicator gun for injecting bone cement into a patient.

It is desirable to prevent air from becoming entrained within the bone cement. It is also desirable to further improve the mixing characteristics of the above-described kit.

SUMMARY OF THE INVENTION

The present invention provides a method and apparatus for mixing bone cement that produces bone cement essentially free from entrained air.

It has been found that in the arrangement described in U.S. Pat. Nos. 5,624,184 and 5,586,821, as the piston plug axially advances in the inner cylinder thereby producing axial movement of the bone cement therewith, the leading edge of the bone cement forms a dome-shaped, or convex, profile, commonly referred to as a "shear flow" profile. The shear flow profile develops because the mixed bone cement exhibits a dough-like consistency which tends to stick to the inner walls of the cylinder, thereby providing resistance to its axial movement. By contrast, the portion of the bone cement toward the center of the cylinder encounters no such resistance with the inner cylinder wall and therefore advances more readily than the bone cement positioned closer to the cylinder wall. Thus, the shear flow profile is caused by the difference in resistance to flow between the bone cement positioned centrally in the cylinder and the bone cement positioned close to the inner wall.

As the bone cement having a shear flow profile advances along the inner cylinder toward the cap opening, the apex of the profile contacts the cap before the portion of the bone cement disposed along the inner wall of cylinder. As a result, a void is produced between the bone cement and the cap, particularly around the cylinder wall. The void contains air which mixes with the bone cement as the bone cement is being expelled through the opening. Of course, as soon as the initial portion of bone cement is expelled through the opening, the profile is flattened by the flat inner surface of the cap as the bone cement advances. Thereafter, the above-described void is no longer present. However, the air initially trapped within the cartridge may undesirably become entrained in the bone cement.

The present invention improves upon a bone cement mixing kit as described in U.S. Pat. Nos. 5,625,184 and 5,586,821 and produces bone cement essentially free of entrained air.

In one form thereof, the present invention provides a method for mixing bone cement under a partial vacuum. The mixing kit includes a mixing cartridge comprised of two telescoping tubular cylinders. The bone cement components are added to the cartridge. A cap is then connected to the cartridge. A vacuum pump is connected to a port on the cap and is operated so as to draw a vacuum in the interior of the cartridge. As vacuum is being drawn in the cartridge using the vacuum pump, the inner cylinder partially retracts, or is drawn into, the outer cylinder. The operation of the vacuum pump is halted when the cartridge has reached the desired vacuum pressure. As a consequence, the inner cylinder automatically stops retracting into the outer cylinder. The components are then mixed.

In a preferred form, the vacuum hose which connects the vacuum pump to the cartridge includes a visual indicator that collapses to indicate that the cartridge has reached the desired vacuum pressure. The operation of the vacuum pump is then halted when the visual indicator collapses, thereby indicating that the cartridge has reached the desired vacuum pressure.

The advantage of the above-described method is that it has been found that it creates a superior environment for mixing the bone cement. As the vacuum pump is being operated, the inner cylinder "seeks its own level" with respect to the outer cylinder until the desired vacuum pressure is reached. This arrangement provides a smaller but adequate volume for mixing the bone cement but, advantageously, provides a smaller available area for unwanted air to occupy.

The present invention provides an improved agitator which provides enhanced mixing, especially in an area proximate the cylindrical walls of the inner and outer cylinders.

In one form thereof, the present invention provides a bone cement mixing apparatus, comprising first and second telescopingly connected cylinders for mixing and dispensing bone cement. The cylinders include respective inner cylinder walls wherein one of the inner walls has an inner diameter greater than an inner diameter of the other inner wall. Also provided is a bone cement agitator having a portion of which is insertable within the cylinders and movable axially therein. The agitator comprises a shaft and a plurality of paddles are connected to an end portion of the shaft and extend generally radially therefrom. The paddles are movable radially and resiliently biased radially outwardly into wiping engagement with the inner cylinder walls. In this arrangement, the paddles flex outwardly to wipe the inner walls of both the inner and outer cylinders when the agitator is reciprocated within the telescopingly connected cylinders.

One advantage of the improved agitator of the present invention is that it enhances the mixing around the walls of both the inner and outer cylinders. This is important because the dry powder component of the unmixed bone cement tends to stick to the cylinder walls and does not get mixed. The wiping engagement provided by the agitator of the present invention reduces this problem.

Another advantage of the agitator of the present invention is that it provides a wiping engagement of both the inner and outer telescoping cylinders, each of which has a different diameter. Further, the resiliently biased paddles do not get "stuck" when moving from one cylinder to the other. Instead, the flexible paddles wipe the inner cylinder wall of the upper (outer) cylinder; then the paddles flex inwardly and wipe the inner cylinder wall of the lower (inner) cylinder. By contrast, a prior art inflexible paddle sized to fit the smaller diameter cylinder cannot provide wiping engagement of the larger cylinder in a telescopic cylinder arrangement.

The present invention provides a means for "squeezing" substantially all of the bone cement from the mixing cartridge by taking advantage of the "shear flow," or dome-shaped, profile formed by the bone cement as it moves axially through the cartridge.

In another form, the present invention comprises a cartridge having a cap on one end thereof which defines an opening therethrough. A piston plug is disposed in the cartridge for axial movement toward the cap to expel the bone cement in the cartridge through the opening. The piston plug has a tapered protrusion thereon which is oriented toward the cap.

In a preferred form, the cap includes a recess whose shape corresponds to the protrusion so that the recess matingly receives the protrusion when the plug is advanced axially toward the cap. Further, the agitator which mixes the bone cement remains within the cartridge while the bone cement is being expelled therefrom. The paddles of the agitator have a shape which corresponds to the recess of the cap and the piston plug whereby the paddles fit snugly therebetween when the piston plug is axially advanced in the cartridge.

An advantage of this arrangement in which the piston plug, the agitator paddles, and the cap have corresponding shapes is that less air is trapped in the cartridge upon the initial expulsion of the bone cement. This is so because the corresponding shapes generally match the convex profile formed by the bone cement so that the size of the air void formed when the bone cement initially exits the opening in the cap is reduced.

Another advantage of the corresponding shapes is that the bone cement is effectively squeezed from the cartridge when the piston plug is fully advanced therethrough. That is, when the piston plug is fully axially advanced in the cartridge, there is little space remaining between the piston plug and the cap. Therefore, the remaining bone cement is effectively squeezed from the cartridge.

The present invention provides an effective mechanism for venting the air contained within a small annular void or "gap" between the agitator shaft and the cap. This venting occurs during the initial expulsion of the bone cement.

In another form thereof, the present invention is an apparatus for mixing and delivering bone cement. The apparatus comprises a cylinder having a cap connected to an end thereof, the cap defining an outlet port therethrough for the discharge of bone cement. A vacuum port is disposed in the cap for attachment thereto of a vacuum pump, which provides a partial vacuum to the cylinder under which the bone cement is mixed. A tubular shaft is disposed in the outlet port, the shaft having one of its ends disposed within the cylinder, the one end having paddles attached thereto. The shaft and the outlet port define an annular gap therebetween. At least one vent extends through the cap. A porous filter encircles the shaft and is positioned intermediate the vent and the annular gap. The porous filter forms a gaseous communication passage connecting the vent to the annular gap. A cement nozzle is attached to the cap. The nozzle and the other end of the shaft define a space therebetween which allows passage of bone cement from the outlet port to the annular gap. In addition to the porous filter, an O-ring encircles the shaft and seals the shaft to an inner surface of the cap at a position inwardly of the porous filter. With the above-described apparatus, air contained within the annular gap can escape through the porous filter and then through the vent when bone cement enters the annular gap; yet the O-ring prevents air contained within the annular gap from entering the cylinder.

The advantage provided by the above-described apparatus of the present invention is that the small amount of air which is contained in the annular gap existing between the agitator shaft and the cap upon the initial expulsion of the bone cement is effectively vented to ambient instead of mixing with the bone cement. This is desirable because when air becomes entrained in bone cement, it forms small voids which are problematic for two reasons. First, the voids could become a fracture site for the bone cement. Second, the voids are a cosmetic problem in that their existence creates a perception that the bone cement is of a lower quality. Advantageously, the present invention provides an apparatus and method which essentially eliminates air entrained in the bone cement.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one exemplary embodiment of the invention, in one form, and such exemplification is not to be construed as limiting the scope of the invention in any manner.

DETAILED DESCRIPTION OF THE INVENTION

Figure 1:
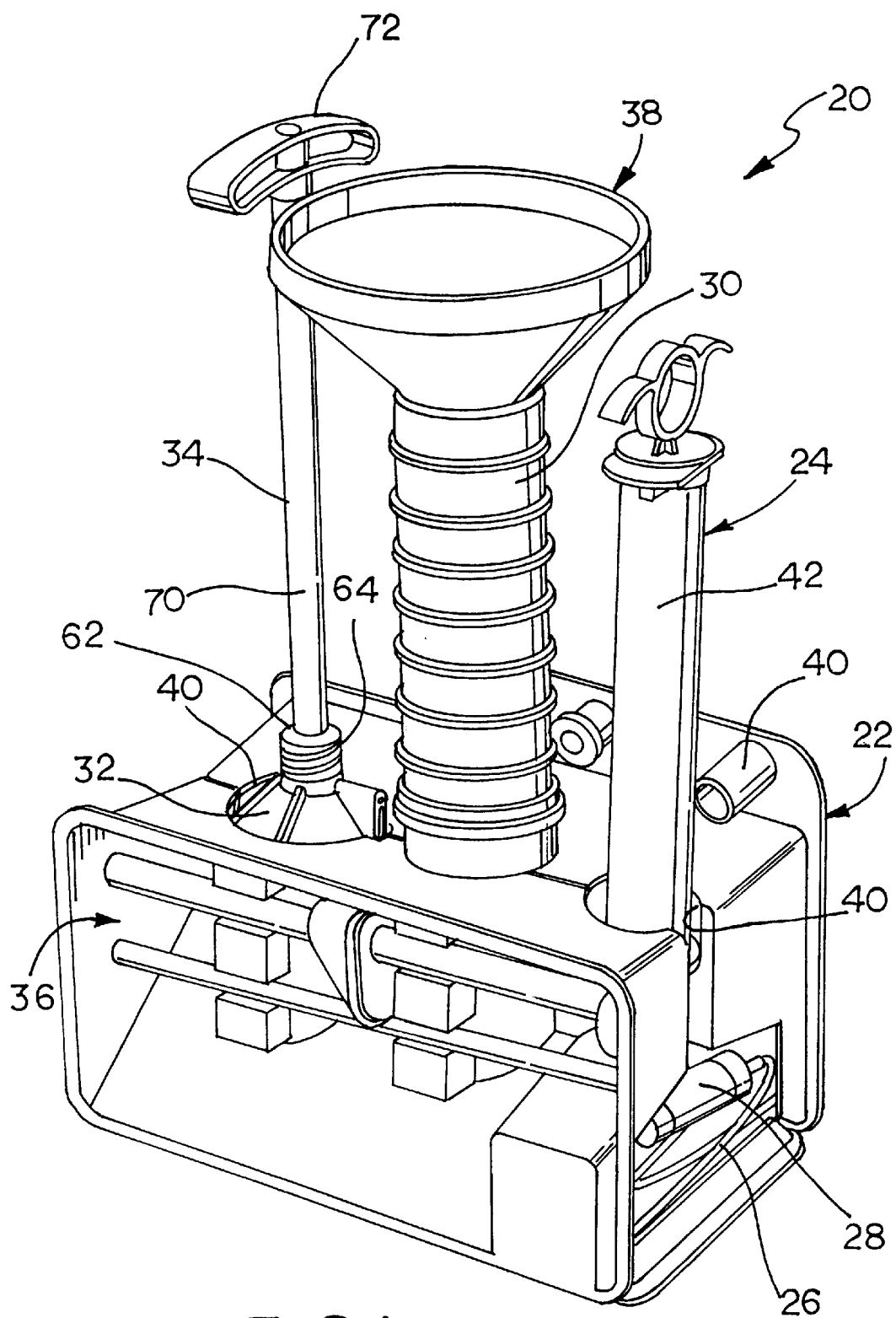
FIG. 1 is a perspective view of the kit including bone cement mixing and injecting components in accordance with the exemplary embodiment of the present invention.

FIG. 1 shows the collection of disposable items of kit 20 of an exemplary implementation of the present invention for use in the preparation of bone cement. Kit 20 consists of the following items: a contoured storage tray 22, vacuum pump 24, connecting tubing 26 having a vacuum indicator 28, a mixing cartridge 30, a cartridge cap 32, break-away agitator 34, cement nozzle and cement nozzle obturatur, which are indicated generally at 36, and a funnel attachment 38. Preferably, tray 22 is constructed from a molded plastic, which has a plurality of contoured recesses 40 within which the various mixing apparatus and delivery accessories are stored.

Typically, the liquid monomer components of the bone cement are provided in ampules (not shown) and the powder copolymers are provided in sealed packets (not shown) although any suitable packaging for the components may be provided with the kit. The liquid monomer and powder copolymer are well-known in the art and are commercially available from a variety of sources.

Figure 2:
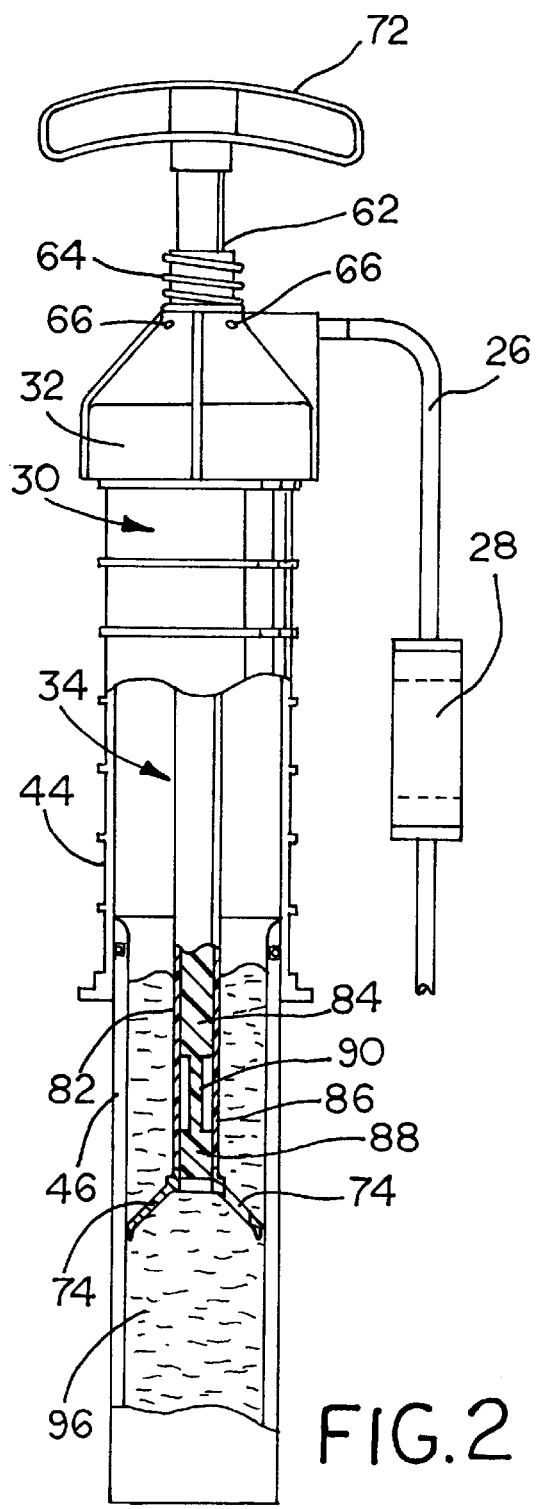
FIGS. 2 and 2A are side views of the mixing cartridge and the connected cap with a portion cut away to illustrate the mixing of the constituent components.
Figure 2A:
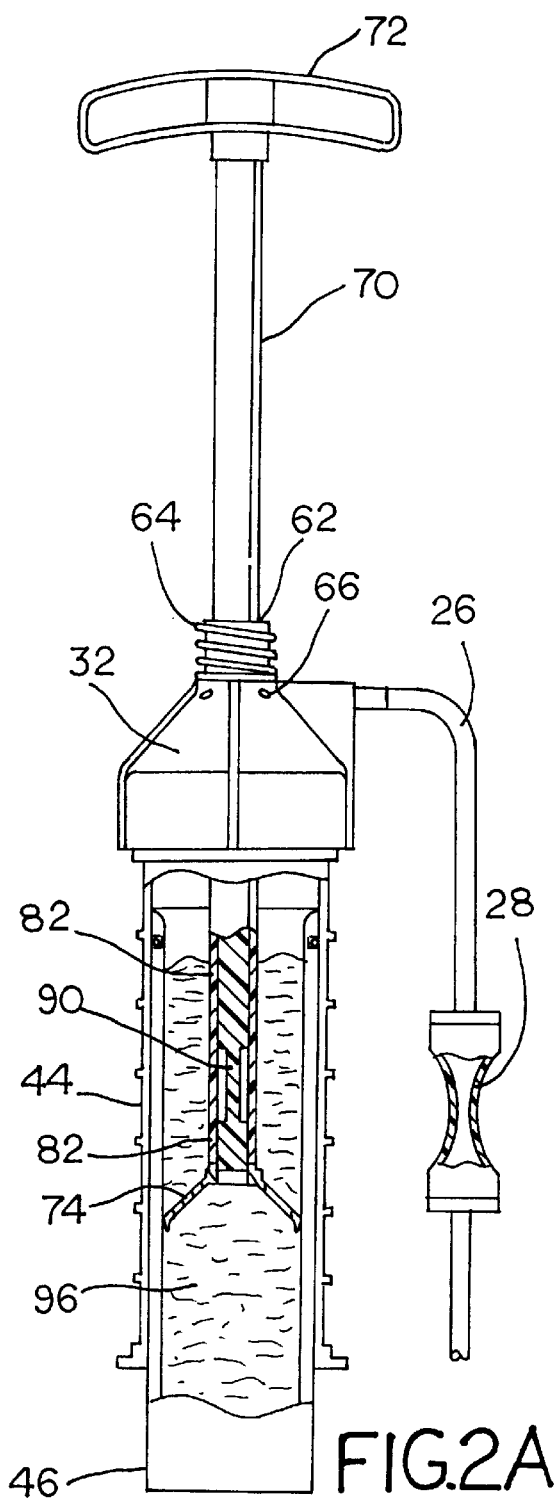

Vacuum pump 24 uses a reciprocated piston design, although any suitable vacuum pump may be included as part of kit 20. Vacuum pump 24 includes a cylindrical body 42 and includes a reciprocating shaft which drives an internal piston (not shown). Vacuum pump 24 also includes a check valve (not shown) to permit air flow through the pump orifice in one direction only. Tubing 26 connects pump 24 to cap 32 when cap 32 is connected to mixing cartridge 30. Tubing 26 includes vacuum indicator 28, which can be a plastic or rubber bulb which collapses under the negative pressure of the vacuum drawn by pump 20 as shown in FIG. 2A.

Mixing cartridge 30 is preferably constructed of disposable plastic, which allows the admixture of the constituent components to be viewed. As shown in FIGS. 2 and 2A, cartridge 30 includes two telescopingly connected tubular cylinders 44 and 46. Both cylinders 44, 46 have open proximal and distal ends. Outer cylinder 44 axially receives inner cylinder 46 in a telescoping configuration. That is, inner cylinder 46 can slide within outer cylinder 44. The outer diameter of inner cylinder 46 is concentrically seated against the inner diameter of outer cylinder 44. The outer peripheral surface of inner cylinder 46 is in a tight but not hermetically sealed engagement with the inner peripheral surface of outer cylinder 44 in a piston-like manner. An air impermeable piston plug 48 (FIG. 4) is disposed within inner cylinder 46 approximate its distal end, so as to close the distal end of inner cylinder 46. Plug 48 is axially slidable within inner cylinder 46 for expelling the mixed cement compound from cartridge 30 when the cartridge is connected to a cement gun. That is, as the cement gun is being operated, piston plug 48 axially advances from the distal end of inner cylinder 46 toward its proximate end (toward cap 32) as shown in FIGS. 4 and 4A.

Figure 4:
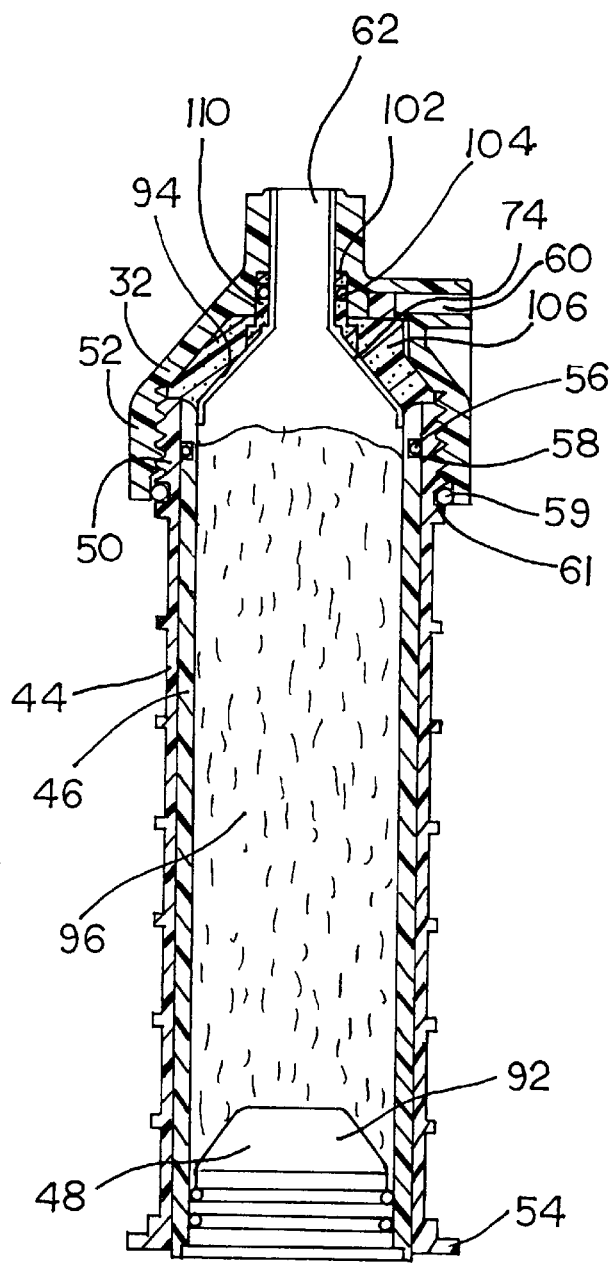
FIGS. 4 and 4A are sectional views of the mixing cartridge in accordance with the exemplary embodiment of the present invention illustrating axial movement of the piston plug.
Figure 4A:
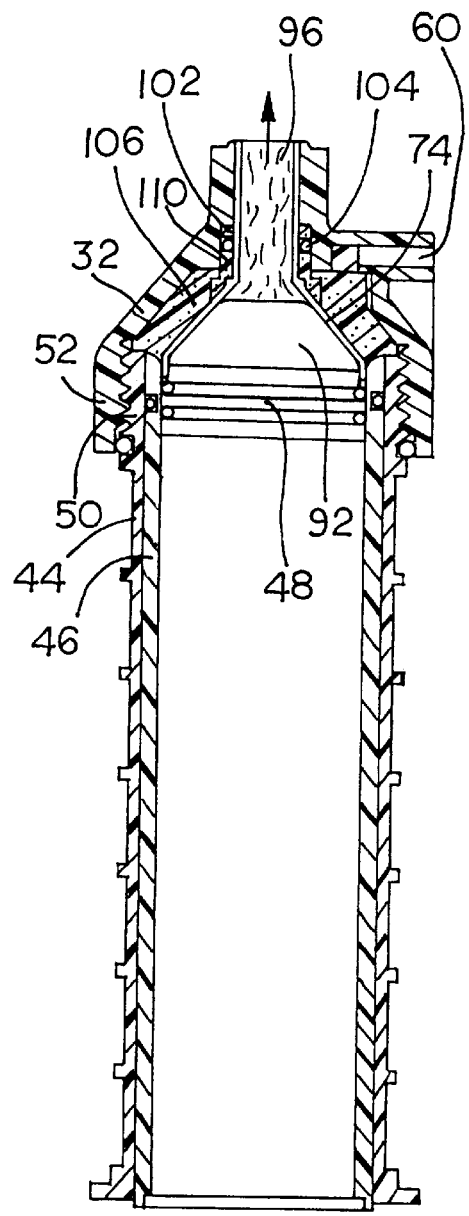

As shown in FIGS. 4 and 4A, outer cylinder 44 includes a threaded outer rim 50 which threadedly engages a threaded annular cap rim 52 of cap 32. While outer cylinder 44 is shown herein as including an outer threaded rim, any suitable connection structure can be employed to provide the connection between cap 32 and outer cylinder 44. Outer cylinder 44 also includes an annular end flange 54 which extends outwardly approximate its open distal end. A hermetic seal is achieved between inner cylinder 46 and outer cylinder 44 by an O-ring 56 seated within annular groove 58 of inner cylinder 46. Cap 32 is hermetically sealed on cylinder 44 by O-ring 59 seated within annular groove 61.

Cap 32 includes a vacuum port 60, which is connectable to vacuum pump 24 by tubing 26. As shown in FIG. 2, cap 32 also includes a centered cement outlet port, or opening 62. Outlet port 62 includes threads 64 for threading engagement of various nozzles 36. Cap 32 also includes vent holes 66 which form part of an air escape passage described hereinbelow.

As shown in FIGS. 2 and 2A, the mixing system of the illustrated embodiment includes an agitator 34 having a shaft 70. A handle 72 is connected to one end portion of shaft 70 and a plurality of paddles 74 are connected to the other end portion of shaft 70. Paddles 74 include holes 75 to aid movement of agitator 34 through the bone cement as is known in the art.

Figure 3:
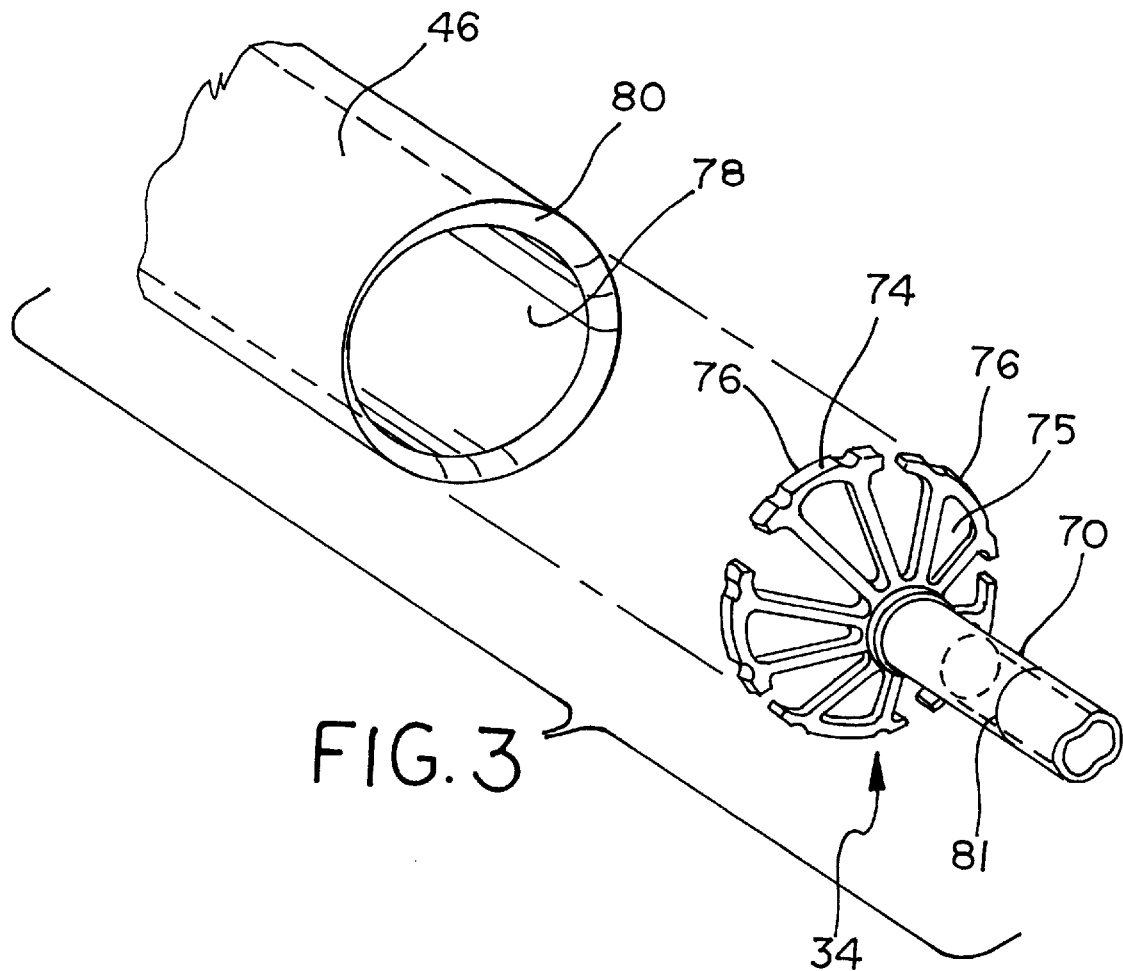
FIGS. 3 and 3A are perspective views of the agitator used with the mixing cartridge.
Figure 3A:
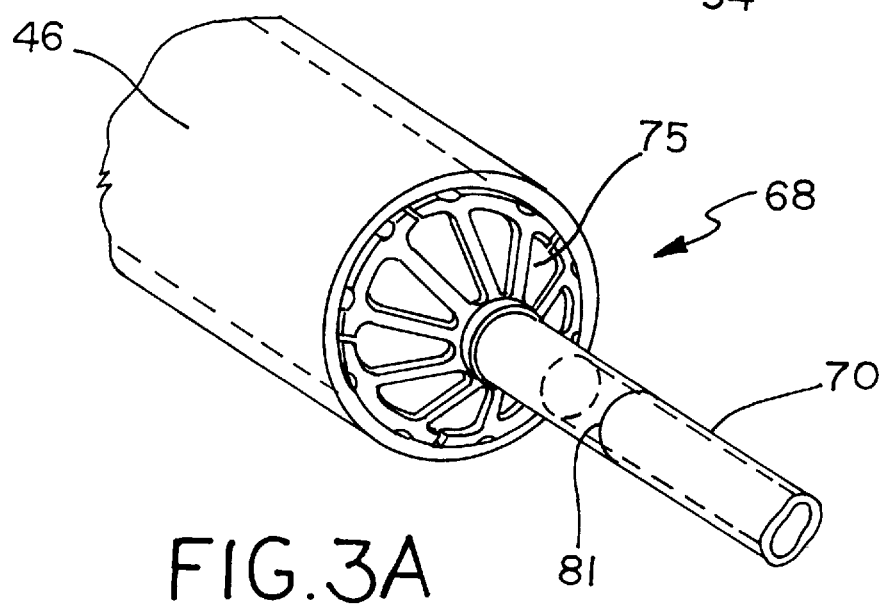

The advantages of the agitator shown in the illustrated embodiment can be better appreciated with reference to FIGS. 3 and 3A. The paddles 74 extend generally radially from the end portion of shaft 70 and are movable radially between a first position which paddles 74 assume when placed within inner cylinder 46 as shown in FIG. 3A, and a second position which the paddles assume when removed from the cylinder as shown in FIG. 3. By comparing FIGS. 3 and 3A, it can be understood that the paddles extend from the shaft a lesser radial distance when inserted in cylinder 46 than when positioned outside of cylinder 46. As further seen with respect to FIGS. 3 and 3A, the outer edges 76 of paddles 74 form a substantially circular shape having a radius which is reduced when the paddles are inserted within cylinder 46. The paddles are formed so that they are resiliently biased radially outwardly toward the position shown in FIG. 3, so that the paddles provide wiping engagement with the inside wall 78 of cylinder 46 when placed therein. Significantly, paddles 74 are also biased outwardly toward cylinder 44, so that a wiping engagement is provided against the inner walls of both cylinders 44 and 46 when the agitator is reciprocated therein (FIG. 2).

The agitator of the present invention is formed from high density polyethylene, but it is to be understood that one of ordinary skill in the art could substitute other suitable materials. Agitator 34 is formed so that paddles 74 naturally occupy their extended position shown in FIG. 3. By selecting a material composition having sufficient elastic properties, the paddles can be resiliently flexed to form the contracted position shown in FIG. 3A. However, the elastic properties of the paddle material cause the paddles to bias outwardly, so that a force is exerted against inner wall 78 when placed within cylinder 46. Similarly, paddles 74 are biased outwardly to provide a wiping engagement of the inner wall of cylinder 44 when placed therein. In the illustrated embodiment, it can be appreciated that paddles 74 need only be capable of withstanding a single use as kit 20 is disposed of after a single use.

As also shown in FIGS. 3 and 3A, inner cylinder 46 includes a flared portion 80 at its proximal end to facilitate insertion of paddles 74. Thus, when the paddles are within cylinder 44 and agitator handle 72 is pressed downwardly, paddles 74 meet flared portion 80 and gradually contract into the position shown in FIG. 3A wherein the radial distance paddle 74 extends from the longitudinal axis of shaft 70 is substantially equal to the radius of the inner cylinder wall 78. Flared portion 80 provides a gradual decrease in radius from the inner wall of the outer cylinder to the smaller diameter inner wall of the inner cylinder so that the paddles do not get stuck when the agitator handle is depressed.

Turning now to FIGS. 2 and 2A, the illustrated embodiment incorporates a break-away agitator assembly essentially the same as that described in U.S. Pat. No. 5,624,184, which is incorporated herein by reference. Shaft 70 includes a tubular outer sleeve 82 and an inner rod 84 axially disposed within sleeve 82. Sleeve 82 is frangible and has a detachable distal end 86. The distal end of inner rod 84 terminates in an integral dumbbell shaped end plug 88. The small diameter of middle segment 90 is positioned approximate an annular notch 81 (FIGS. 3 and 3A), or score line, disposed in shaft sleeve 82. The annular notch 81 forms a radius around sleeve 82 about which sleeve 82 fractures when shaft 70 is fully extended from cartridge 30. The hollow distal end 86 of sleeve 82 remains within outlet port 62 of cap 32 to provide a passage for the mixed cement compound to be expelled.

With reference to FIG. 4, piston plug 48 includes an integral protrusion 92 thereon which is oriented toward cap 32. Generally, protrusion 92 is formed in a tapered shape designed to match the shape of cap 32 and closely resemble the convex, or "shear flow," profile of the bone cement as the bone cement is axially advanced through cartridge 30 by movement of piston plug 48. Thus, while protrusion 92 is shown in FIG. 4 as being frustoconically shaped, it is to be understood that protrusion 92 could be formed into other similar shapes, such as a dome, bullet-shape and the like.

With further reference to FIG. 4, cap 32 includes a recess 94 whose shape corresponds to protrusion 92. Thus, recess 94 matingly receives protrusion 92 when plug 48 is axially advanced toward cap 32 as shown in FIG. 4A. While recess 94 is shown in FIG. 4 as being frustoconically shaped, it is to be understood that recess 94 could be formed into other similar shapes, such as a dome, bullet-shape and the like. Recess 94 is shaped correspondingly to protrusion 92. Paddles 74 also comprise a shape which corresponds to protrusion 92 and recess 94, whereby cap 32 and piston plug 48 matingly receiving paddles 74 therebetween when plug 48 is axially advanced toward cap 32 as shown in FIG. 4A. In the embodiment illustrated in FIGS. 4 and 4A, cap 32 having recess 94, piston plug 48 and agitator paddles 74 all comprise matching frustoconical shapes, the advantages of which in operation are described hereinbelow.

Figure 5:
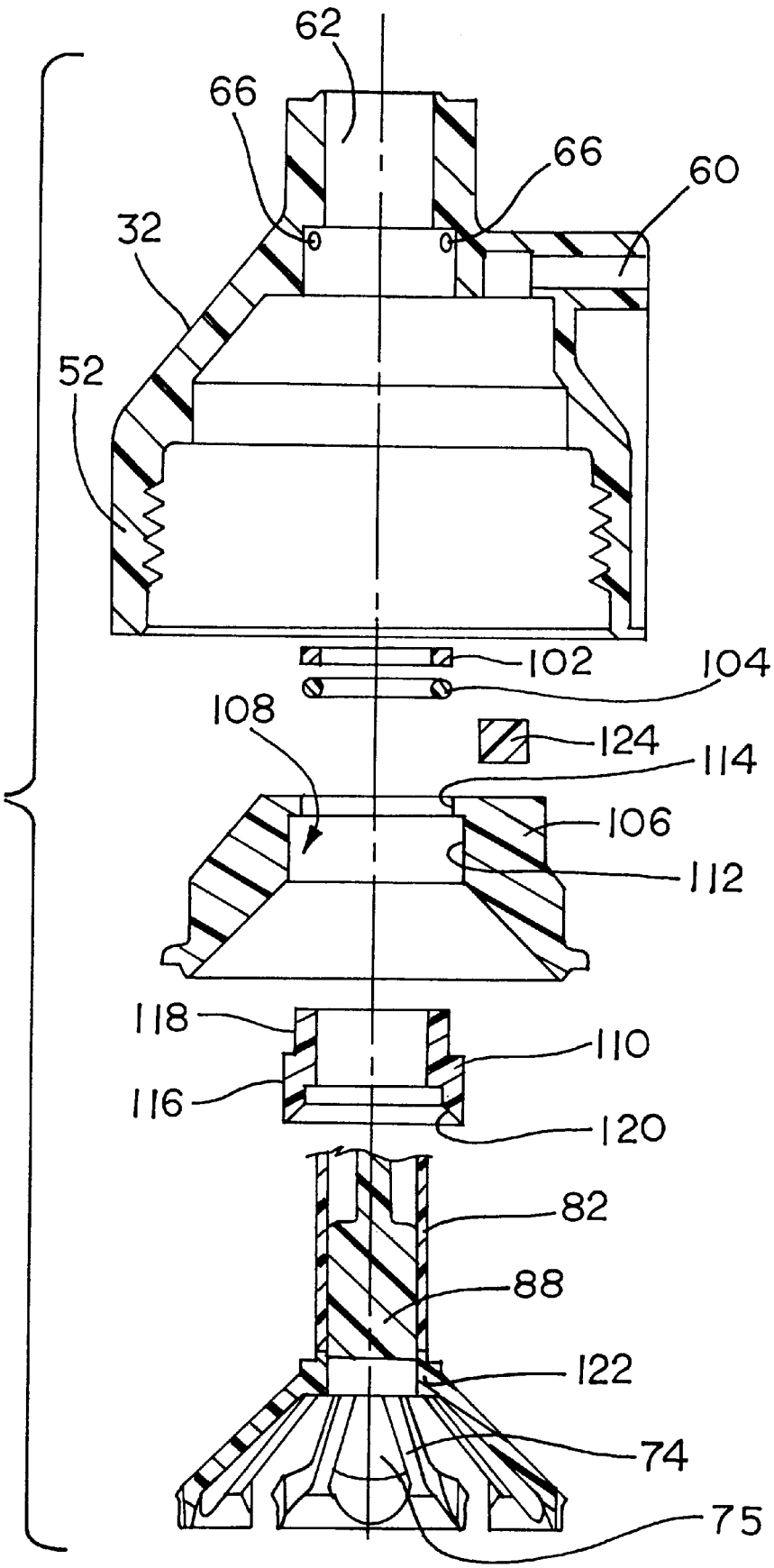
FIG. 5 is an exploded fragmentary sectional view of the cap assembly and agitator.
Figure 6:
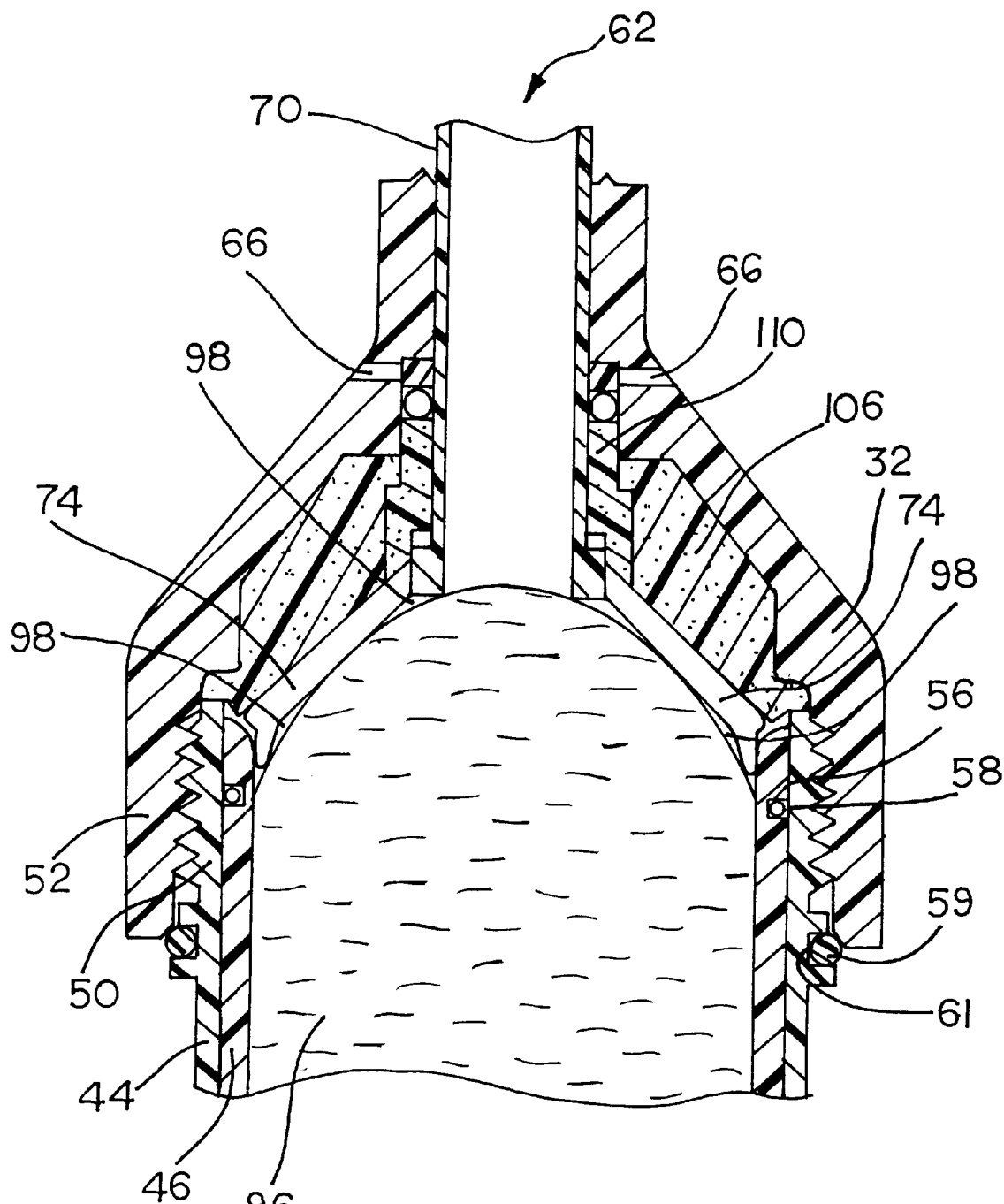
FIG. 6 is a fragmentary sectional view of the cap assembly showing the bone cement about to be expelled therefrom.

The illustrated embodiment of the present invention provides a novel air escape passage for venting substantially all of the air contained within the confines of the cap to ambient. As shown in FIGS. 5 and 6, vents 66 extend through cap 32 and lead to shaft 70. A cylindrical porous filter 102 encircles shaft 70 and forms a semi-permeable membrane which allows passage of air but not bone cement therethrough. It has been found that ultra-high molecular weight polyethylene performs satisfactorily as a material for porous filter 102. Positioned inwardly in cap 32 with respect to porous filter 102 is an O-ring 104 which also encircles shaft 70. O-ring 104, preferably made of silicone, seals shaft 70 to an inner surface of cap 32, thereby preventing passage of air into cartridge 30 during the expulsion of bone cement, as explained hereinbelow.

As further shown in FIG. 5, the interior of cap 32 widens to provide additional space for top filter 106. Filter 106 allows air to be drawn out of the system via vacuum port 60 without pulling out dry powder or mixed cement. Top filter 106 includes a two-tiered opening 108 which receives retaining ring 110. As can be understood with reference to FIGS. 5 and 6, top filter 106 includes inner annular surfaces 112 and 114 which match outer annular surfaces 116 and 118 of retaining ring 110, respectively. The bottom inner portion of retaining ring 110 includes a frustoconical portion 120 which mates with base 122 of paddle assembly 74. Cap 32 also includes absorbent filter 124 which absorbs any monomer that is pulled through the top filter 106 before it can move into the tubing set.

Figure 7:
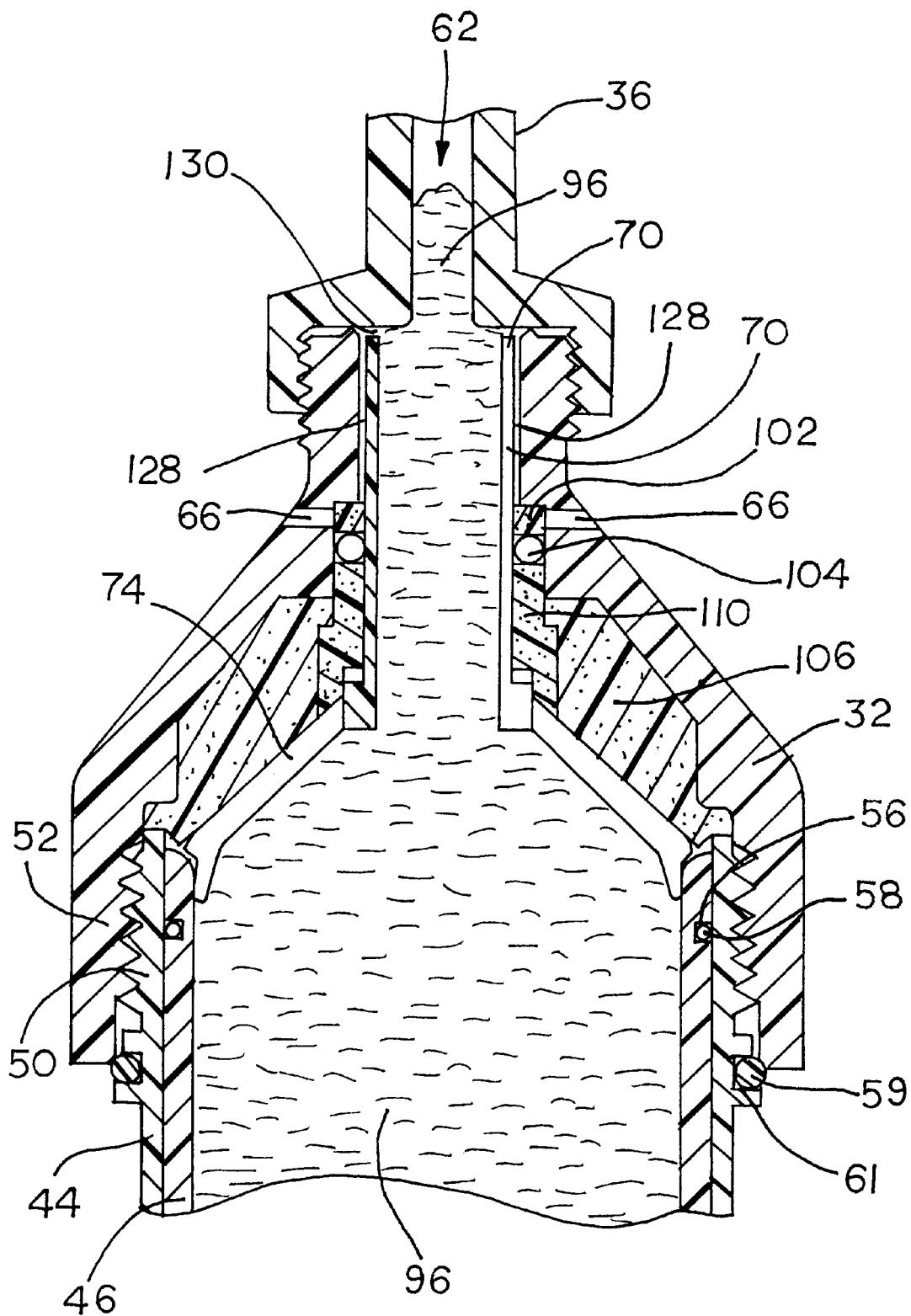
FIG. 7 is a fragmentary sectional view of the cap assembly showing an annular gap between the cap and the agitator shaft which contains air during the initial expulsion of bone cement.

As shown in FIG. 7, after agitator shaft 70 is broken off, nozzle 36 is threaded onto cap 32. There exists a small annular gap 128 between agitator shaft 70 and the inner annular surface of cap 32 as shown in FIG. 7. The size of gap 128 shown in FIG. 7 has been exaggerated for illustrative purposes. There also exists a small space 130 between the bottom of nozzle attachment 36 and the end (broken off) portion of agitator shaft 70. Space 130 allows passage of bone cement from outlet port 62 into annular gap 128. Thus, with reference to FIG. 7, it can be appreciated that annular gap 128 is in fluid communication with outlet port 62 because of the existence of space 130. It can be further appreciated that annular gap 128 is in gaseous communication with vents 66 because porous filter 102 is disposed intermediate annular gap 128 and vents 66. Stated another way, porous filter 102 forms a gaseous communication passage connecting vents 66 to annular gap 128. While porous filter 102 in the illustrated embodiment is a cylindrical member which encircles shaft 70, it is to be understood that one of ordinary skill in the art would readily recognize that other configurations of a porous filter may be utilized, provided that one or more porous filters prevent bone cement from seeping from vents 66.

FIGS. 1–7 demonstrate the use of kit 20 of the illustrated embodiment in the preparation of bone cement. Kit 20 is packaged in an external packaging (not shown) with funnel attachment 38 connected to cartridge 30. Cartridge 30 is packaged in tray 22 in its extended mixing position; i.e., inner cylinder 46 is fully extended from outer cylinder 44, for the convenience of the user. The cement constituent components (not shown) of the cement are poured into cartridge 30 through funnel attachment 38. Once the proper volumes of the various constituent components of the cement have been poured into the cartridge, funnel attachment 38 is removed and discarded. Cap 32 is then removed from tray 22 and attached to cartridge 30. Vacuum pump 24, tubing 26 and vacuum indicator 28 are also removed from tray 22 and connected to vacuum port 60 of cap 32. Once cap 32 and vacuum pump 24 are connected to cartridge 30 as shown in FIGS. 2 and 2A, a vacuum is drawn within cartridge 30 by manually reciprocating the shaft of vacuum pump 24. Vacuum indicator 28 collapses to indicate that the cartridge has reached the desired vacuum pressure.

Concurrent with the drawing of the vacuum within cartridge 30, inner cylinder 46 is drawn within outer cylinder 44. This is so because, while inner cylinder 46 fits snugly within outer cylinder 44, cartridge 30 provides no locking mechanism maintaining inner cylinder 46 in its fully extended position. Thus, as vacuum is drawn within cartridge 30, inner cylinder 46 "seeks its own level" within outer cylinder 44. That is, there is no predetermined position that cylinder 46 must occupy within cylinder 44 when vacuum indicator 28 indicates that the desired level of vacuum has been achieved within the cartridge. It has been found that such an arrangement provides an excellent mixing environment for the bone cement. When vacuum indicator 28 collapses to indicate the proper vacuum pressure within cartridge 30, inner cylinder 46 is partially retracted within cylinder 44 to a position wherein there is sufficient room for mixing the bone cement using agitator 34, yet there is reduced room within cartridge 30 for trapped air to occupy. The reduction in volume provides less mixing space and therefore reduces the opportunity for air to be mixed in the cement. As a result, the embodiment illustrated achieves a reduction in entrained air within the bone cement.

After the desired vacuum is achieved within cartridge 30, the constituent components of the cement are mixed manually by reciprocating agitator 34 in a manner well-known in the art. Advantageously, the self-biasing action of paddles 74 against inner wall 78 of inner cylinder 46 provides enhanced mixing around wall 78 of inner cylinder 46. Additionally, the paddles provide a self-biasing action against the inner wall of cylinder 44 when the paddles are reciprocated therein. The advantage of the agitator in the illustrated embodiment is that it provides a wiping engagement of both telescoping cylinders, 44 and 46, each of which has a different diameter. Further, the resiliently biased paddles do not get "stuck" when moving from one cylinder to the other because cylinder 46 includes a flared end which eases entry of paddles 74 as shown in FIG. 3. In operation, the flexible paddles wipe the inner cylinder wall of cylinder 44; then the paddles flex inwardly as the handle is pressed downwardly and wipe the inner cylinder wall of cylinder 46.

Upon completion of mixing, vacuum pump 24 may be removed and the vacuum within cartridge 30 is thereby released. Cartridge 30 is then compressed so that inner cylinder 46 is fully retracted within outer cylinder 44 as shown in FIG. 4 for use in a cement injector gun (not shown). Thence, distal end 86 of sleeve 82 of the agitator is broken off and discarded. When agitator 34 is broken off, plug 88 is pulled from the cap and outlet port 62 is opened. A suitable cement nozzle 36 is then affixed to outlet port 62 and cartridge 30 is inserted into an applicator gun (not shown). A bone cement injector gun suitable for use with the illustrated embodiment is shown and described in U.S. Pat. No. 5,638,997 which is owned by the assignee of the present invention and is incorporated herein by reference.

Figure 6A:
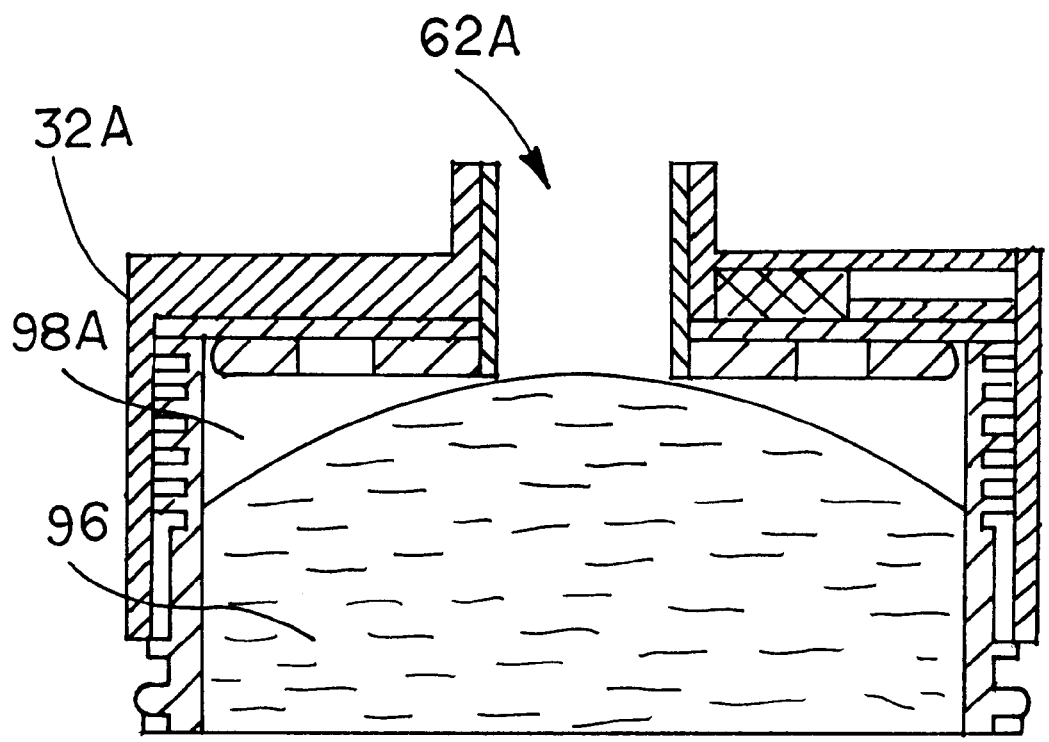
FIG. 6A is a fragmentary sectional view of a prior art cap assembly showing bone cement about to be expelled therefrom.

It has been found that as piston plug 48 (FIG. 4) axially advances through inner cylinder 46 pushing the bone cement therewith, a convex, or "shear flow," profile develops at the leading portion of the bone cement as shown in FIG. 6. Bone cement has a dough-like consistency which sticks to the inner cylinder wall of the cartridge so that there is greater resistance to axial movement around the cylinder wall than in the middle of the cartridge. The convex profile produced by axially advancing the bone cement can be problematic in a prior art cartridge like that shown in FIG. 6A. As shown in FIG. 6A, when the apex of bone cement 96 reaches outlet port 62A, a void 98A that contains air is formed between bone cement 96 and cap 32A. The air within void 98A may "fold" into bone cement 96 as the bone cement is expelled through outlet port 62A, thereby producing unwanted porosity in the bone cement. This phenomenon occurs only during the initial expulsion of bone cement 96 and the quantity of air involved is limited. It is nonetheless desirable to reduce the size of the void. As shown in FIG. 6, the illustrated embodiment reduces the size of void 98 by use of the specially shaped cap 32, piston plug 48 and paddles 74.

When cement nozzle 36 is attached to cap 32 and bone cement 96 advances into nozzle 36 as shown in FIG. 7, air contained in annular gap 128 must be vented to ambient. As the bone cement continues to advance through the cartridge and nozzle 36, it also seeps from outlet port 62 through space 130 and into gap 128, thereby moving the air contained within annular gap 128 through porous filter 102 and out of the cap through vents 66. Advantageously, porous filter 102 allows air but not bone cement to pass therethrough. After the initial expulsion of bone cement from cartridge annular gap 128 becomes completely filled with bone cement, all of the air formerly contained therein having escaped to ambient as described above. If an air escape passage were not provided, the air in gap 128 would become trapped and could be pushed into the bone cement being expelled from the cartridge. O-ring 104 provides a fluid seal between cap 32 and shaft 70 so that air cannot enter cartridge 30.

While this invention has been described as having a exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A bone cement mixing apparatus, comprising:
   first and second telescopingly connected cylinders for mixing and dispensing bone cement, said first and second cylinders including respective inner cylinder walls wherein one of said inner walls has an inner diameter greater than an inner diameter of the other inner wall; and
   a bone cement agitator having a portion of which is insertable within said cylinders and movable axially therein, said agitator comprising:
   a shaft; and
   a plurality of paddles connected to an end portion of said shaft and extending generally radially therefrom, said paddles being movable radially and resiliently biased radially outwardly into wiping engagement with said first and second inner walls, whereby said paddles can flex outwardly to wipe said inner walls when said agitator is reciprocated within said telescopingly connected cylinders.

2. The apparatus of claim 1, wherein said paddles form a frustoconical shape.

3. The apparatus of claim 1, wherein said paddles each includes an opening therein for passage of bone cement therethrough while mixing.

4. A method for mixing bone cement, said method comprising the steps of:

placing bone cement components in a cartridge, the cartridge including a first cylinder slidably disposed within a second cylinder, the first cylinder initially being extended from the second cylinder;

installing a cap on a proximal end of the second cylinder and connecting a vacuum pump to a vacuum port on the cap, whereby vacuum can be drawn within the cartridge;

drawing vacuum in the cartridge by operating the vacuum pump and thereby causing the first cylinder to be drawn into the second cylinder;

halting the operation of the vacuum pump when the pressure within the cartridge reaches a desired level, thereby stopping the first cylinder from being further drawn into the second cylinder; and then mixing the bone cement components within the cartridge under the vacuum created within the cartridge.

5. The method according to claim 4, wherein the first cylinder automatically stops moving relative to the second cylinder upon the pressure within the cartridge reaching the predetermined level.

6. The method according to claim 4, further comprising the steps of:

releasing the vacuum within the cartridge;

installing a cement nozzle on the cap;

advancing the bone cement through an outlet port in the cap and through the nozzle; and venting substantially all of the air contained within the cap to ambient.

7. An apparatus for mixing and delivering bone cement, said apparatus comprising:

a cylinder;

a cap on one end of said cylinder and defining an outlet port therethrough; and a piston plug disposed in said cylinder for axial movement in said cylinder toward said cap to expel the bone cement in said cylinder through said outlet port; said piston plug having a tapered protrusion thereon which is oriented toward said cap, wherein said cap includes a recess corresponding in shape to said protrusion, said recess matingly receiving said protrusion when said plug is moved axially toward said cap, whereby the bone cement is squeezed from said cylinder;

an agitator for mixing the bone cement, said agitator comprising a shaft extending through said outlet port, a first end of said shaft disposed within said cylinder; and a plurality of paddles connected to said first end of said shaft and extending radially therefrom for mixing the bone cement, said paddles forming a shape which corresponds to said piston plug and said cap, whereby said cap and said piston plug matingly receive said paddles therebetween when said piston plug is moved axially toward said cap.

8. The apparatus of claim 7, wherein said cap, seid paddles and said toward said cape.

* * * * *